United States Patent [19]

Wagner

[11] Patent Number: 4,824,661

[45] Date of Patent: Apr. 25, 1989

[54] COMPOSITION FOR ORAL HYGIENE

[75] Inventor: Helmar R. Wagner, Darmstadt-Arheilgen, Fed. Rep. of Germany

[73] Assignee: Blendax-Werke R. Schneider GmbH & Co., Mainz, Fed. Rep. of Germany

[21] Appl. No.: 903,761

[22] Filed: Sep. 5, 1986

[30] Foreign Application Priority Data

Sep. 14, 1985 [DE] Fed. Rep. of Germany ....... 3532860

[51] Int. Cl.$^4$ .................. A61K 7/16; A61K 7/18; A61K 33/34
[52] U.S. Cl. ..................... 424/52; 424/48; 424/49; 424/141
[58] Field of Search .................. 424/48–58, 424/140, 141

[56] References Cited

U.S. PATENT DOCUMENTS

| | | | |
|---|---|---|---|
| 4,006,218 | 2/1977 | Sipos | 424/54 |
| 4,022,880 | 5/1977 | Vinson et al. | 424/49 |
| 4,332,791 | 6/1982 | Raaf et al. | 424/54 |
| 4,339,429 | 7/1982 | Raaf et al. | 424/54 |
| 4,622,220 | 11/1986 | Frosch | 424/49 |
| 4,656,031 | 4/1987 | Lane et al. | 424/49 |

OTHER PUBLICATIONS

Becker et al. (I) C.A. 96: 57601H (1982) of EPO 38867, Nov. 4, 1981.
Becker et al. (II) C.A. 96: 57602H (1982) of EPO 38868, Nov. 4, 1981.
Saxton C.A. 104: 135881Z (1986) of EPO 16189 Nov. 21, 1985.
Gilbert C.A. 106: 382147 (1987) of Caries Res. 21(1): 29–36 (1987).

*Primary Examiner*—S. K. Rose
*Attorney, Agent, or Firm*—Birch, Stewart, Kolasch & Birch

[57] ABSTRACT

A composition for oral hygiene with efficacy against dental plaque contains as active substances a mixture of copper compounds and 2,4,4'-trichloro-2'-hydroxydiphenyl ether, preferably in an amount of from about 0.05 to about 1.5% by weight.

6 Claims, No Drawings

COMPOSITION FOR ORAL HYGIENE

The present invention relates to a composition for oral hygiene, especially a tooth and mouth care agent having a dental plaque preventing or disminishing activity, containing a mixture of copper compounds and 2,4,4'-trichloro-2'-hydroxydiphenyl ether as active ingredients.

It is known that the copper cation has an inhibiting effect on dental plaque formation when solutions containing copper compounds are typically brought into contact with teeth (AADR-Abstracts 1979, No. 117; Caries Research, Vol. 18, 1984, 434–439).

These compounds supplying copper ions do not have the disadvantages known from other plaque-inhibiting compounds on the basis of antimicrobial substances, as e.g. quaternary ammonium compounds or chlorhexidine salts, particularly discoloration of the teeth after long-term use.

However, up to the present time, they have not been incorporated into toothpastes and similar compositions containing further active ingredients and auxiliary substances because either the copper salts were caused to be inactivated by these substances or they did not maintain their activity at every desired pH-value.

In European Published Patent Application Nos. 38,867 and 38,868 toothpaste compositions are described which contain copper compounds in an active form. This is effected by an optimum selection of the respective polishing agent.

Although these compositions been shown to be active against dental plaque, it is desirable not to be restricted to certain components in the selection of the polishing agent and the pH-value.

For this reason, there was a demand for a tooth and mouth care agent which supplies copper ions with plaque-inhibiting activity that is not limited to the presence of special polishing agents, but even having an improved efficiency.

This difficult problem was surprisingly solved by adding to a tooth and mouth care agent containing copper ions, 2,4,4'-trichloro-2'-hydroxydiphenyl ether in an amount of about 0.02, particularly 0.05 to about 1.5, especially about 0.1% by weight, calculated on the total composition.

The amount of copper compounds used in the compositions for oral hygiene according to the present invention should be dosed in such a way that about 0.001 to about 5% by weight of Cu, calculated to the total composition, are present.

A preferred amount is between 0.05 to 1.5%, particularly about 0.5% of Cu.

In principle, all toxicologically safe, mucosa-compatible copper ions, even those which are water-soluble only to a certain degree, are suitable as compounds for supplying copper ions.

Inorganic salts are for example:

Copper chloride, $CuCl_2$, and its dihydrate; copper fluoride, $CuF_2$, and its dihydrate; copper fluorosilicate, $CuSiF_6$, and its hexahydrate; copper sulfate, $CuSO_4$, and its pentahydrate; copper nitrate and its tri- and hexahydrate, respectively, as well as copper salts, which are not as common, such as bromides, bromates, chlorates, iodates and fluorophosphates.

Preferred copper salts of organic acids are acetate, formate, benzoate, citrate, tartrate, lactate, malate, mandelate, sorbate, pentothenate, gluconate, phytate, glycerophosphate, cinnamate, butyrate, propionate, laurate, oxalate and salicylate.

Also suitable are the copper salts of amino acids, such as glycinate or glutamate. A particularly preferred amino acid salt is copper aspartate.

The animal tests described below prove the superior efficiency of a toothpaste containing copper sulfate (0.05% by weight calculated to copper) and 2,4,4'-trichloro-2'-hydroxydiphenyl ether compared to toothpastes containing copper sulfate and/or 2,4,4'-trichloro-2'-hydroxyphenyl ether alone as well as an untreated control group:

20 day old Osborne Mendel rats are divided into 4 groups with 16 animals each and each of the animals received the plaque standard diet 2000° F.

At the beginning of the test the initial plaque status of each test animal is determined. Then, the animals are inoculated with 0.1 ml of a standardized bacterial suspension of Actinomyces viscious OMZ 105. Further inoculations are carried out each week.

The treatment of the test animals with the preparations to be investigated begins at the 23rd life day, twice daily 0.1 ml test preparation/test animal are applied by a syringe. After 4 weeks the animals are sacrificed and the plaque formation is investigated on the 2 first buccal surfaces and the first 4 lingual surfaces of the molars 1 and 2 in the upper jaw; i.e., 12 surfaces per animal.

The evaluation is carried out after coloration with erythrosin solution according to the following scheme:
0: no plaque
1: up to ⅓ of the surface is covered with plaque.
2: up to ⅔ of the surface are covered with plaque.
3: more than ⅔ of the surface are covered with plaque.

The corresponding points are added and an average value (x) is calculated.

| Group | Result $\overline{x}$ | |
|---|---|---|
| 1 | 18.56 | +/− 1.27 |
| 2 | 12.73 | +/− 1.65 |
| 3 | 18.79 | +/− 1.24 |
| 4 | 23.00 | +/− 1.68 |

Composition of toothpastes

Group 1: According to example A, however without copper sulfate.
Group 2: According to example A.
Group 3: According to example A, however without 2,4,4'-trichloro-2'-hydroxydiphenyl ether
Group 4: Untreated control group.

These results show the superiority of the synergistic combination according to the present invention of copper compounds and 2,4,4'-trichloro-2'-hydroxydiphenyl ether.

EXAMPLE A

| | |
|---|---|
| α-Alumina trihydrate (particle size distribution approx. 1–15 μm) | 58.50 (% by weight) |
| Sorbitol solution (70%) | 25.50 |
| Xanthum gum | 0.60 |
| Sodium monofluorophosphate | 0.80 |
| Saccharin sodium | 0.10 |
| Preservative | 0.30 |
| Sodium lauryl sulfate | 0.40 |
| Flavour mixture | 0.10 |
| Copper sulfate.$5H_2O$ | 0.20 |

| | |
|---|---|
| -continued | |
| 2,4,4'-Trichloro-2'-hydroxydiphenyl ether | 0.10 |
| Water | ad 100.00 |

The compositions for oral hygiene according to the present invention may be used in various application forms. Toothpastes, either opaque or gel-like transparent, mouthwashes and chewing gum are preferred; however, any other application form like mouth spray, sucking or chewing tablets, or tooth powders is suitable for this purpose.

A toothpaste may be opaque or transparent. Transparent toothpastes contain polishing agents having the same refraction index as the carrier material.

Especially suitable polishing agents are alumina, especially as trihydrate, such as α-alumina trihydrate, having a preferred particle size distribution between about 1 and about 20, especially about 10 μm, and calcium carbonate.

However, it is also possible to use toothpastes based on other carrier materials containing as polishing agents e.g. alkali aluminum silicates, e.g. zeolites A as disclosed in European Published Patent Application Nos. 2,690 and 3,023, different calcium phosphates such as dicalcium orthophosphate, dihydrates or water-free, tricalcium phosphate, calcium pyrophosphate, insoluble alkali metaphosphates, and the like, silicas of different modifications, such as silica xerogels, hydrogels or precipitated silica, or powdered plastic materials such as polymethyl methacrylate with a particle size distribution between about 0.5 and about 5 μm.

Also mixtures of the mentioned polishing substances may be used, e.g., a mixture of α-alumina hydrate and/or calcium carbonate and synthetic zeolite A in a ratio of about 1:1.

The percentage of polishing agent in a toothpaste according to the present invention is preferably between about 20 and about 60% by weight of the total composition.

It is also possible to use the usual surface-active agents in toothpastes in amounts of up to 2.5% by weight of the total composition.

Suitable synthetic surface-active agents are e.g. alkyl sulfates, alkyl ether sulfates, olefin sulfonates, sodium lauroyl sarcosinate, or ampholytic, nonionic, or cationic compounds or soaps such as alkali salts from lauric acid, myristic acid, palmitic acid, stearic acid, or mixtures thereof, e.g., coconut oil fatty acids or tallow fatty acids.

Also essential constituents of toothpastes are moisturizers normally present in amounts between from about 10 and about 35% by weight. Suitable moisturizers are glycerol, diols like 1,4-butanediol or 1,2-propanediol or sugar alcohols like sorbitol, mannitol or xylitol, and also polyethylene glycols with low molecular weights.

Also contained in toothpastes are thickening agents, whose amount is between about 0.25 and about 5% by weight of the total composition.

Preferred thickening agents are carboxymethyl cellulose and its alkali salts, especially sodium carboxymethyl cellulose, hydroxyalkyl celluloses like hydroxymethyl cellulose and hydroxyethyl cellulose, methyl cellulose, natural gums such as tragant, Gum arabicum, caraya gum, guar gum, xanthum gum, and Irish moss, synthetic polyelectrolytes such as alkali salts of polyacrylic acid as well as inorganic thickening agents, especially colloidal magnesium aluminum silicate or colloidal silica.

The compositions for oral hygiene according to the present invention may also contain additional active ingredients. Especially the incorporation of the well-known caries-prophylactic fluorides is advantageous, preferably in such an amount that the concentration of the pure fluorine in the composition is between from about 0.05 to about 1% by weight, particularly between 0.1 and 0.5% by weight of the total composition.

Suitable fluorine compounds are the different salts of monofluorophosphoric acid such as sodium, potassium, lithium, calcium, and aluminum mono- and difluorophosphate as well as the various ionic fluorides, particularly alkali fluorides like sodium, lithium, potassium, and ammonium fluoride, stannous fluoride, manganese fluoride, copper fluoride, zirconium fluoride, and aluminum fluoride as well as mixtures or adducts of these fluorides, e.g. alkali manganese fluorides.

Further materials which can be used in the preparations for oral hygiene according to the present invention are further plaque-inhibiting substances for such as zinc salts, substances preventing the formation of dental calculus, such as hydroxyethane-1,2-diphosphonic acid or alkylene amino tetramethylene phosphonic acids and their water-soluble salts, allantoin, azulen, etc.

A review of the compositions to be used in toothpastes as well as of other materials usually applied for the preparation of dental care agents and the manufacturing methods for these compositions are given in the monography of M. S. Balsam and E. Sagarin, "Cosmetics—Science and Technology", 2nd Ed., Vol. 1, p. 423 to 533 (1972), which is included by reference.

The following examples should characterize the principle of the invention:

EXAMPLE 1

| Toothpaste | |
|---|---|
| α-Alumina trihydrate (particle size about 1–15 μm) | 58.50 (% by weight) |
| Sorbitol solution (70%) | 25.50 |
| Xanthan gum | 0.60 |
| Sodium monofluorophosphate | 0.80 |
| Saccharin sodium | 0.10 |
| Preservative | 0.30 |
| Sodium lauryl sulfate | 0.40 |
| Flavour mixture | 0.10 |
| Copper aspartate | 0.26 |
| 2,4,4'-Trichloro-2'-hydroxydiphenyl ether | 0.05 |
| Water | ad 100.00 |

EXAMPLE 2

| Toothpaste | |
|---|---|
| Synthetic zeolite A ($Na_{12}(AlO_2)_{12}(SiO)_2)_{12}\cdot 27H_2O$) | 24.00 (% by weight) |
| Dicalcium orthophosphate | 10.00 |
| Carboxymethyl cellulose | 1.20 |
| Sodium lauryl sulfate | 2.00 |
| Glycerol | 6.00 |
| Sorbitol | 15.00 |
| Preservative | 0.30 |
| Flavour mixture | 1.00 |
| Colloidal silica | 1.55 |
| Saccharin sodium | 0.05 |
| Sodium monofluorophosphate | 0.80 |
| Copper aspartate | 0.25 |
| 2,4,4'-Trichloro-2'-hydroxydiphenyl | 0.08 |

-continued

| Toothpaste | |
|---|---|
| ether | |
| Water | ad 100.00 |

EXAMPLE 3

| Toothpaste | |
|---|---|
| Irish moss | 0.50 (% by weight) |
| Xanthan gum | 0.50 |
| Glycerol | 7.50 |
| Sorbitol | 22.00 |
| Copper formiate.4H$_2$O | 0.30 |
| Copper fluoride (CuF$_2$) | 0.25 |
| Sodium lauroyl sarcosinate | 1.40 |
| Cured Melamine-formaldehyde condensate (mean particle diameter 1–10 μm) | 28.50 |
| Titanium dioxide | 0.50 |
| Saccharin sodium | 0.10 |
| Flavour mixture | 1.00 |
| p-Hydroxybenzoic acid methylester | 0.10 |
| p-Hydroxybenzoic acid n-propylester | 0.05 |
| 2,4,4'-Trichloro-2'-hydroxydiphenyl ether | 0.22 |
| Desalted water | 37.30 |

EXAMPLE 4

| Toothpaste | |
|---|---|
| Xanthan gum | 1.20 (% by weight) |
| Glycerol | 15.00 |
| Sorbitol | 12.00 |
| Copper salicylate (Cu(C$_7$H$_5$O$_3$)$_2$.4H$_2$O) | 1.00 |
| 2,4,4'-Trichloro-2'-hydroxydiphenyl ether | 0.12 |
| Silica xerogel (Syloid ® AL 1, surface about 800 m$^2$/g) | 16.00 |
| Colloidal silica (Aerosil ®) | 3.00 |
| Titanium dioxide | 0.50 |
| Flavour mixture | 1.00 |
| Saccharin sodium | 0.16 |
| Trisodium citrate | 0.25 |
| p-Hydroxybenzoic acid ethyl ester | 0.20 |
| Desalted water | ad 100.00 |

EXAMPLE 5

| Toothpaste | |
|---|---|
| Glycerol | 19.00 (% by weight) |
| Sorbitol (70%) | 7.00 |
| Polyethylene glycol 300 | 3.00 |
| Copper lactate hydrate | 1.20 |
| Stannous fluoride (SnF$_2$) | 0.40 |
| Hydroxyethane-1,1-diphosphonic acid, trisodium salt | 1.25 |
| Bromochlorophene | 0.05 |
| 2,4,4'-Trichloro-2'-hydroxyphenyl ether | 0.06 |
| Benzoic acid | 0.15 |
| Dehydracetic acid | 0.10 |
| p-Hydroxybenzoic ester n-propylester | 0.05 |
| Polymethyl methacrylate powder (mean particle diameter 3–8 μm) | 20.00 |
| Silica-xerogel (Syloid ® 70, surface about 290 m$^2$/g) | 8.50 |
| Colloidal silica (Aerosil ®) | 1.20 |
| Sodium lauryl ether sulfate (25% in ethanol) | 10.00 |

-continued

| Toothpaste | |
|---|---|
| Xanthan gum | 0.80 |
| Desalted water | ad 100.00 |

EXAMPLE 6

| Chewing gum | |
|---|---|
| Gum base | 30.00 (% by weight) |
| Sorbitol | 25.00 |
| Xylitol | 20.00 |
| Saccharin sodium | 0.30 |
| Zinc acetate.2H$_2$O | 2.30 |
| 2,4,4'-Trichloro-2'-hydroxydiphenyl ether | 0.30 |
| Copper sulfate.2H$_2$O | 0.30 |
| Glycerol | 2.00 |
| Flavour mixture | 3.80 |
| Ascorbic acid | 1.00 |
| Fructose | 15.00 |

EXAMPLE 7

| Mouthwash concentrate | |
|---|---|
| Flavour mixture | 5.00 (% by weight) |
| Copper aspartate | 2.50 |
| Zinc citrate.2H$_2$O | 0.25 |
| 2,4,4'-Trichloro-2'-hydroxydiphenyl ether | 0.35 |
| Nonionic emulsifier | 1.80 |
| n-Propanol | 5.00 |
| 1-Methoxypropanol(−2) | 35.00 |
| Glycerol | 8.50 |
| Phenyl salicylate | 0.55 |
| Saccharin sodium | 0.30 |
| Water | ad 100.00 |

Before use, the concentrate is diluted with water in a ratio of about 1:4.

EXAMPLE 8

| Chewing gum | |
|---|---|
| Gum base | 30.00 |
| Sorbitol | 25.00 |
| Xylitol | 20.00 |
| Saccharin sodium | 0.30 |
| Copper fluoride | 0.50 |
| Copper sulfate.2H$_2$O | 1.30 |
| 2,4,4'-Trichloro-2'-hydroxydiphenyl ether | 2.00 |
| Glycerol | 2.00 |
| Flavour mixture | 2.70 |
| Ascorbic acid | 1.00 |
| Fructose | 15.00 |

I claim:

1. A composition for oral hygiene comprising a copper salt in an amount corresponding to from about 0.001 to 5% by weight of copper and from about 0.02 to 1.5% by weight of 2,4,4'-trichloro-2'-hydroxydiphenyl ether, wherein the weight percentages are based on the total weight of the composition.

2. The composition of claim 1, which comprises from about 0.05 to 0.5% by weight of 2,4,4'-trichloro-2'-hydroxydiphenyl ether.

3. The composition of claim 1, which comprises about 0.1% by weight of 2,4,4'-trichloro-2'-hydroxydiphenyl ether.

4. The composition of claim 1, wherein the copper salt is selected from the group consisting of copper chloride, copper chloride dihydrate, copper fluoride, copper fluoride dihydrate, copper fluorosilicate, copper fluorosilicate hexahydrate, copper sulfate, copper sulfate pentahydrate, copper nitrate, copper nitrate trihydrate, copper nitrate hexahydrate, copper bromide, copper bromate, copper chlorate, copper iodate, copper fluorophosphate, copper acetate, copper formate, copper benzoate, copper citrate, copper tartrate, copper lactate, copper malate, copper mandelate, copper sorbate, copper pantothenate, copper gluconate, copper phytate, copper glycerophosphate, copper cinnamate, copper butyrate, copper propionate, copper laurate, copper oxalate, copper salicylate, copper glycinate, copper glutamate and copper aspartate.

5. The composition of claim 1, wherein said composition is in the form of a toothpaste, mouthwash, chewing gum, mouth spray, tablet or powder.

6. The composition of claim 1 comprising a cariesprophylactic fluoride.

* * * * *